US00PP35446P2

(12) United States Plant Patent
de Vos

(10) Patent No.: US PP35,446 P2
(45) Date of Patent: Oct. 31, 2023

(54) ***HYDRANGEA* PLANT NAMED 'HYLV18535'**

(50) Latin Name: *Hydrangea paniculata*
Varietal Denomination: HYLV18535

(71) Applicant: KWEKERIJ LENDERT de VOS B.V., Reeuwijk (NL)

(72) Inventor: Lendert de Vos, Reeuwijk (NL)

(73) Assignee: KWEKERIJ LENDERT de VOS B.V., Reeuwijk (NL)

( * ) Notice: Subject to any disclaimer, the term of this patent is extended or adjusted under 35 U.S.C. 154(b) by 0 days.

(21) Appl. No.: 18/101,112

(22) Filed: Jan. 24, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP22,330 P2 * 12/2011 Wood ..... A01H 6/48
Plt./250

* cited by examiner

*Primary Examiner* — June Hwu
(74) *Attorney, Agent, or Firm* — C. Anne Whealy

(57) ABSTRACT

A new and distinct cultivar of *Hydrangea* plant named 'HYLV18535', characterized by its relatively compact, upright to broadly spreading plant habit; moderately vigorous growth habit; freely branching habit; strong and sturdy stems; freely flowering habit; panicles with greenish white-colored sterile flowers that become red in color with subsequent development; and good garden performance.

2 Drawing Sheets

Figure 1:
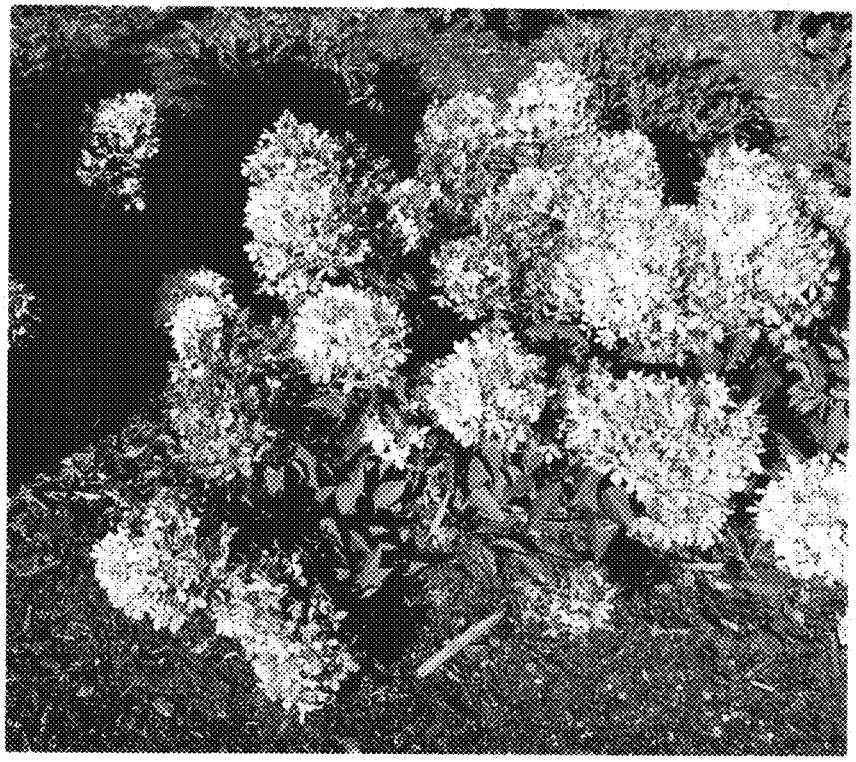

Botanical designation: *Hydrangea paniculata.*
Cultivar denomination: 'HYLV18535'.

CROSS-REFERENCED TO CLOSELY-RELATED APPLICATIONS

An European Community Plant Breeder's Rights application for this plant was filed by the Applicant/Assignee of the instant application, Kwekerij Lendert de Vos of Reeuwijk, The Netherlands on Jan. 25, 2022, application number 2022/0237. Foreign priority is not claimed to this European Plant Breeder's Rights application.

BACKGROUND OF THE INVENTION

The present invention relates to a new and distinct cultivar of *Hydrangea* plant, botanically known as *Hydrangea paniculata*, commercially referred to as a Paniculated *Hydrangea* and hereinafter referred to by the name 'HYLV18535'.

The new *Hydrangea* plant is a product of a planned breeding program conducted by the Inventor in Reeuwijk, The Netherlands. The objective of the breeding program is to create new compact and strong *Hydrangea* plants with attractive inflorescences and good postproduction longevity.

The new *Hydrangea* plant originated from an open-pollination during the summer of 2016 of a proprietary selection of *Hydrangea paniculata* identified as code number P13502, not patented, as the female, or seed, parent with an unknown selection of *Hydrangea paniculata* as the male, or pollen, parent. The new *Hydrangea* plant was discovered and selected as a single flowering plant from within the progeny of the stated open-pollination in a controlled greenhouse environment in Reeuwijk, The Netherlands in August, 2018.

Asexual reproduction of the new *Hydrangea* plant by terminal vegetative cuttings since August, 2018 in a controlled greenhouse environment in Reeuwijk, The Netherlands has shown that the unique features of this new *Hydrangea* plant are stable and reproduced true to type in successive generations of asexual reproduction.

SUMMARY OF THE NEW PLANT

Plants of the new *Hydrangea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HYLV18535'. These characteristics in combination distinguish 'HYLV18535' as a new and distinct *Hydrangea* plant:

1. Relatively compact, upright to broadly spreading plant habit.
2. Moderately vigorous growth habit.
3. Freely branching habit.
4. Strong and sturdy stems.
5. Freely flowering habit.
6. Panicles with greenish white-colored sterile flowers that become red in color with subsequent development.
7. Good garden performance.

Plants of the new *Hydrangea* can be compared to plants of the female parent selection. Plants of the new *Hydrangea* differ primarily from plants of the female parent selection in the following characteristics:

1. Plants of the new *Hydrangea* are more compact than plants of the female parent selection.

2. Inflorescences of plants of the new *Hydrangea* are not as dense as inflorescences of plants of the female parent selection.

Plants of the new *Hydrangea* can be compared to plants of *Hydrangea paniculata* 'Jane', disclosed in U.S. Plant Pat. No. 22,330. In side-by-side comparisons, plants of the new *Hydrangea* differ primarily from plants of 'Jane' in the following characteristics:

1. Plants of the new *Hydrangea* are more upright than and not as outwardly spreading as plants of 'Jane'.
2. Plants of the new *Hydrangea* are denser than and not as open as plants of 'Jane'.
3. Stems of plants of the new *Hydrangea* are stronger than stems of plants of 'Jane'.
4. Inflorescences of plants of the new *Hydrangea* are not as dense as inflorescences of plants of 'Jane'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HYLV18535' grown in an outdoor nursery.

Figure 2:
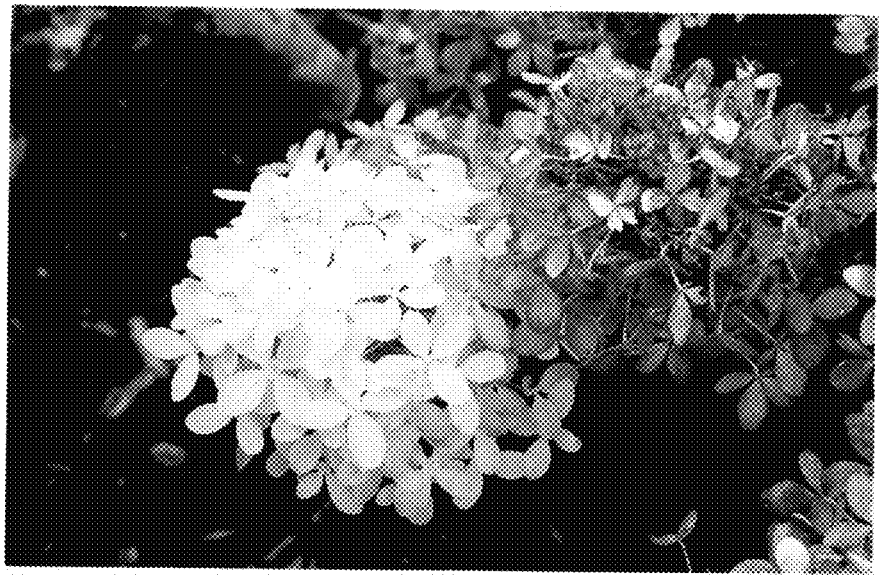

The photograph at the top of the second sheet (FIG. 2) is a close-up view of typical inflorescences of 'HYLV18535'.

Figure 3:
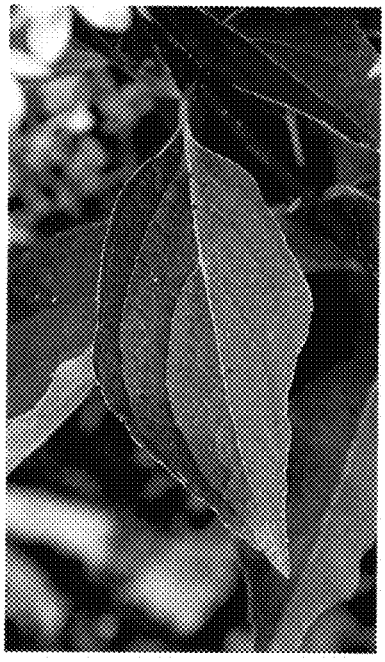

The photograph at the bottom of the second sheet (FIG. 3) is a close-up view of typical leaves of 'HYLV18535'.

DETAILED BOTANICAL DESCRIPTION

Plants used in the aforementioned photographs and in the following description were grown during the late summer in ground beds in an outdoor nursery in Reeuwijk, The Netherlands and under cultural practices typical of commercial *Hydrangea* production. During the production of the plants, day temperatures ranged from 18° C. to 32° C., night temperatures ranged from 12° C. to 20° C. Plants of the new *Hydrangea* were pruned in the spring and pinched in the early summer. Plants were three years old when the photographs and description were taken. In the following description, color references are made to The Royal Horticultural Society Colour Chart, 2015 Edition, except where general terms of ordinary dictionary significance are used. Paniculated *Hydrangea* plants are not typically treated with aluminum sulfate to "blue" the flower color.

Botanical description: *Hydrangea paniculata* 'HYLV18535'.

Parentage:

*Female, or seed, patent.*—Proprietary selection of *Hydrangea paniculata* identified as code number P13502, not patented.

*Male, or pollen, patent.*—Unknown selection of *Hydrangea paniculata*, not patented.

Propagation:

*Type cutting.*—By vegetative terminal cuttings.

*Time to initiate roots, summer.*—About 16 days at temperatures ranging from 20° C. to 30° C.

*Time to produce a rooted young plant, summer.*—About four months at temperatures ranging from 20° C. to 30° C.

*Root description.*—Medium in thickness to thick; fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Relatively compact; upright to broadly outwardly spreading and mounding plant habit; flattened broadly obovate in overall shape; strong and sturdy stems; moderately vigorous growth habit and moderate growth rate; about one year from propagation are required to produce small finished plants.

*Plant height.*—About 47.5 cm.

*Plant diameter or area of spread.*—About 69.5 cm.

Lateral branch description:

*Branching habit.*—Freely branching habit with about 32 lateral branches developing per plant; pinching is not required, but will enhance lateral branch development.

*Length.*—About 26.4 cm.

*Diameter.*—About 4.5 mm.

*Internode length.*—About 5.1 cm.

*Strength.*—Strong, sturdy.

*Aspect.*—Erect to about 50° from vertical.

*Texture.*—Sparsely pubescent; becoming woody with subsequent development.

*Color, developing.*—Close to 147C.

*Color, fully developed.*—Close to N199A, N199B and 200C; when woody, close to 197B, 197C, 199C, N199B and 200C to 200D.

*Lenticels.*—Density: Sparse. Length: About 1 mm. Diameter: About 0.5 mm. Color: Close to N199D.

Leaf description:

*Arrangement.*—Opposite or in whorls of three, simple.

*Length.*—About 7.5 cm.

*Width.*—About 3.9 cm.

*Shape.*—Elliptic to close to ovate; moderately to strongly carinate.

*Apex.*—Apiculate.

*Base.*—Attenuate to close to rounded.

*Margin.*—Senate.

*Texture and luster, upper surface.*—Sparsely pubescent; matte.

*Texture and luster, lower surface.*—Sparsely pubescent; slightly glossy.

*Venation pattern.*—Pinnate.

*Color.*—Developing leaves, upper surface: Close to a blend of 143A and 146A. Developing leaves, lower surface: Close to 146B. Fully developed leaves, upper surface: Close to NN137B; venation, close to 152B. Fully developed leaves, lower surface: Close to 147B; venation, close to 151D.

*Petioles.*—Length: About 1.1 cm. Diameter: About 1.75 mm. Texture and luster, upper and lower surfaces: Sparsely pubescent; slightly glossy. Color, upper surface: Close to 152B. Color, lower surface: Close to 146D.

Flower description:

*Flower type and habit.*—Showy rotate sterile flowers and small, inconspicuous rotate fertile flowers arranged on terminal panicles; panicles irregular conical to broadly conical in shape; sterile flowers face upright, outwardly to drooping and fertile flowers face mostly upright.

*Fragrance.*—Faintly to moderately fragrant; sweet and pleasant.

*Natural flowering season.*—In the garden, plants flower continuously from the midsummer to late summer in The Netherlands.

*Flower longevity.*—Good postproduction longevity; sterile flowers maintain good substance for about six weeks on the plant, sterile flowers persistent; fertile flowers last for about five days on the plant, fertile flowers not persistent.

*Quantity of flowers.*—Freely flowering habit; about 325 sterile flowers per panicle and about 440 fertile flowers per panicle.

*Panicle height.*—About 16.4 cm.

*Panicle diameter.*—About 15 cm.

*Panicle peduncles.*—Length: About 15.2 cm. Diameter: About 3 mm. Strength: Moderately strong. Aspect: Primary peduncles, mostly erect; lateral peduncles, about 50° from primary peduncle axis. Texture: Sparsely pubescent. Color: Close to 145C.

*Sterile flower buds.*—Length: About 6 mm. Diameter: About 1.2 cm. Shape: Broadly cup-shaped. Color: Close to a blend of 150C and 154D.

*Fertile flower buds.*—Length: About 4 mm. Diameter: About 3 mm. Shape: Broadly obovate. Color: Immature corolla, close to NN155A to NN155B; immature calyx, close to 157D.

*Sterile flower diameter.*—About 3 cm.

*Sterile flower depth (height).*—About 4 mm.

*Fertile flower diameter.*—About 8 mm.

*Fertile flower depth (height).*—About 7 mm.

*Petals, sterile flowers.*—Quantity and arrangement: Four in a single whorl. Length: About 2.5 mm. Width: About 1.25 mm. Shape: Narrowly ovate, concave. Apex: Acute. Base: Cuneate. Margin: Entire. Texture and luster, upper surface: Smooth, glabrous; moderately glossy. Texture and luster, lower surface: Smooth, glabrous; slightly glossy. Color: When opening and fully opened, upper surface: Close to NN155D; color does not change with subsequent development. When opening and fully opened, lower surface: Close to NN155D; color does not change with subsequent development.

*Petals, fertile flowers.*—Quantity and arrangement: Five in a single whorl. Length: About 3 mm. Width: About 1.5 mm. Shape: Ovate, slightly to moderately concave. Apex: Acute. Base: Cuneate. Margin: Entire. Texture and luster, upper surface: Smooth, glabrous; moderately glossy. Texture and luster, lower surface: Smooth, glabrous; slightly glossy. Color: When opening and fully opened, upper surface: Close to a blend of NN155D and 157D; color does not change with subsequent development. When opening and fully opened, lower surface: Close to a blend of NN155D and 157D; color does not change with subsequent development.

*Sepals, sterile flowers.*—Quantity and arrangement: Typically four, or occasionally three or five, arranged in a single whorl. Length: About 1.7 cm. Width: About 9.5 mm. Shape: Obovate to narrowly obovate to elliptic. Apex: Obtuse. Base: Narrowly cuneate. Margin: Entire. Texture and luster, upper and lower surfaces: Smooth, glabrous; matte. Color: When opening, upper and lower surfaces: Close to 150D. Fully opened, upper surface: Close to a blend of 150D and 157A; towards the apex, slightly tinged with close to 181D; with subsequent development, color becoming closer to 181B and 181C. Fully opened, lower surface: Close to 157B; towards the margins and apex, slightly tinged with close to 181D; with subsequent development, color becoming closer to 148C and 148D and towards the margins, close to 181C.

*Sepals, fertile flowers.*—Quantity and arrangement: Five in a single whorl. Length: About 1 mm. Width: About 1.25 mm. Shape: Broadly deltoid. Apex: Broadly acuminate. Base: Broadly cuneate. Margin: Entire. Texture and luster, upper and lower surfaces: Smooth, glabrous; matte. Color: When opening and fully opened, upper surface: Close to 157C; color does not change with subsequent development. When opening and fully opened, lower surface: Close to 157C; color does not change with subsequent development.

*Pedicels, sterile flowers.*—Length: About 2.2 cm. Diameter: About 0.8 mm. Strength: Moderately strong. Aspect: About 30° to 60° from main peduncle axis. Texture and luster: Moderately to densely pubescent; matte. Color: Close to 157C.

*Pedicels, fertile flowers.*—Length: About 5 mm. Diameter: About 0.75 mm. Strength: Moderately strong. Aspect: About 30° from vertical. Texture and luster: Moderately pubescent; matte. Color: Close to 157D.

*Reproductive organs, sterile flowers.*—Stamens: Quantity per flower: Eight. Filament length: About 2 mm. Filament color: Close to 155C. Anther shape: Oblong. Anther length: About 0.5 mm. Anther color: Close to 158D. Pollen amount: Scarce. Pollen color: Close to 155D. Pistils: Pistil quantity per flower: One; deformed. Pistil length: About 1 mm. Stigma shape: Pointed. Stigma color: Close to 155A. Style length: About 0.5 mm. Style color: Close to 154C to 154D. Ovary color: Close to 145C.

*Reproductive organs, fertile flowers.*—Stamens: Quantity per flower: Ten. Filament length: About 4.5 mm. Filament color: Close to NN155D. Anther shape: Oblong. Anther length: About 0.5 mm. Anther color: Close to 158D. Pollen amount: Scarce. Pollen color: Close to 155D. Pistils: Pistil quantity per flower: Two or occasionally, three. Pistil length: About 1.5 mm. Stigma shape: Club-shaped. Stigma color: Close to 155C. Style length: About 0.5 mm. Style color: Close to 145D. Ovary color: Close to 147D.

*Seeds.*—To date, seed development has not been observed on plants of the new *Hydrangea.*

Pathogen & pest resistance: Plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HYLV18535' as illustrated and described.

* * * * *